United States Patent [19]

Suchy

[11] 4,276,305

[45] Jun. 30, 1981

[54] CYCLOPROPANE CARBOXYLIC ACID ESTERS AND CYCLOPROPANE(THIO)-CARBOXYLIC ACID ESTERS

[75] Inventor: Milos Suchy, Pfaffhausen, Switzerland

[73] Assignee: Hoffmann-La Roche Inc., Nutley, N.J.

[21] Appl. No.: 115,313

[22] Filed: Jan. 25, 1980

[30] Foreign Application Priority Data

Feb. 9, 1979 [CH] Switzerland .......................... 1290/79
May 18, 1979 [CH] Switzerland .......................... 4674/79
Jan. 11, 1980 [CH] Switzerland ............................ 214/80

[51] Int. Cl.³ .................... C07C 153/09; A01N 9/24; C07C 69/74; A01N 53/00
[52] U.S. Cl. ............................... 424/301; 260/455 R; 260/465 D; 560/124; 424/304; 424/305

[58] Field of Search ..................... 260/455 R; 424/301

[56] References Cited

U.S. PATENT DOCUMENTS

| | | | |
|---|---|---|---|
| 3,673,237 | 6/1972 | Janiak | 424/301 X |
| 3,816,501 | 6/1974 | Henrick et al. | 260/455 R |
| 3,849,466 | 11/1974 | Henrick et al. | 260/455 R |
| 4,112,116 | 9/1978 | Pallos | 424/301 |

*Primary Examiner*—Joseph P. Brust
*Attorney, Agent, or Firm*—Jon S. Saxe; George M. Gould; William M. Farley

[57] ABSTRACT

Cyclopropane carboxylic acid esters and cyclopropane(thio)-carboxylic acid, esters, processes for their preparation, as well as pesticidal compositions containing these esters as the active ingredients and methods for the use of the pesticidal compositions are disclosed.

9 Claims, No Drawings

CYCLOPROPANE CARBOXYLIC ACID ESTERS AND CYCLOPROPANE(THIO)-CARBOXYLIC ACID ESTERS

SUMMARY OF THE INVENTION

This invention is directed to esters of the formula

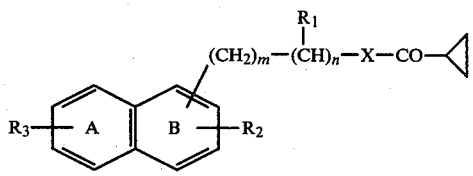

wherein $R_1$ is lower alkyl, halo-substituted lower alkyl, lower alkenyl, lower alkynyl, cyano, phenyl, substituted phenyl wherein the substituents are selected from the group consisting of halogen, methyl, ethyl, methoxy, ethoxy and nitro; $R_2$ is hydrogen, halogen, alkyl of from 1 to 3 carbons, alkoxy of from 1 to 3 carbons, alkenyloxy of 3 or 4 carbons, alkynyloxy of 3 or 4 carbons or nitro; $R_3$ is hydrogen, alkyl of from 1 to 3 carbons or alkoxy of from 1 to 3 carbons; X is oxygen or sulphur; m is zero or an integer from 1 to 3 and n is zero or 1; wherein one or both of rings A and B can be saturated and wherein m and n cannot simultaneously be zero, and with the further proviso that $R_2$ and $R_3$ cannot simultaneously be hydrogen when X is oxygen, m is 1 and the methylene group bearing the cyclopropane carboxylic acid or cyclopropane(thio)carboxylic acid moiety is bonded at the β-position of the naphthalene ring, as well as processes for their preparation. This invention is also directed to pesticidal compositions containing, as the active ingredient, a compound of formula I and methods for use of these pesticidal compositions.

DETAILED DESCRIPTION OF THE INVENTION

Compounds of the formula

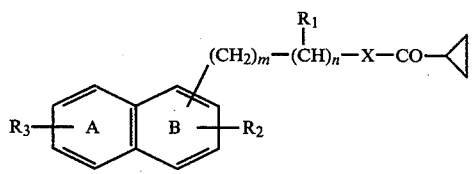

wherein $R_1$ is lower alkyl, halo-substituted lower alkyl, lower alkenyl, lower alkynyl, cyano, phenyl, substituted phenyl wherein the substituents are selected from the group consisting of halogen, methyl, ethyl, methoxy, ethoxy and nitro; $R_2$ is hydrogen, halogen, alkyl of from 1 to 3 carbons, alkoxy of from 1 to 3 carbons, alkenyloxy of 3 or 4 carbons, alkynyloxy of 3 or 4 carbons or nitro; $R_3$ is hydrogen, alkyl of from 1 to 3 carbons or an alkoxy of from 1 to 3 carbons, X is oxygen or sulphur; m is zero or an integer of from 1 to 3 and n is zero or 1; wherein one or both of rings A and B can be saturated and wherein m and n cannot simultaneously be zero, and with the further proviso that $R_2$ and $R_3$ cannot simultaneously be hydrogen when X is oxygen, m is 1 and the methylene group bearing the cyclopropane carboxylic acid or cyclopropane(thio)-carboxylic acid moiety is bonded to the β-position of the naphthalene ring, are active as pesticides. They are especially suited for the control of insects and acarina.

This invention is also directed to pesticidal compositions which contain, as the active ingredient, one or more of the compounds of formula I and to methods for the use of these pesticidal compositions.

This invention is also directed to processes for the preparation of compounds of formula I.

As used herein, the term "lower alkyl" includes alkyl of from 1 to 6 carbons such as methyl, ethyl, propyl, isopropyl, butyl, isobutyl and tert.butyl. The term "lower alkenyl" includes straight- and branched-chain alkenyl of from 2 to 6 carbons such as vinyl, propenyl, butenyl, isobutenyl, pentenyl and the like. The term "lower alkynyl" includes straight- and branched-chain alkynyl of up to 6 carbon atoms such as propargyl, butynyl, isobutynyl, pentynyl and the like. The term "halogen" includes fluorine, chlorine, bromine and iodine unless stated otherwise.

The compounds of formula I wherein $R_2$ and $R_3$ are not simultaneously hydrogen when m is 1 and the methylene group bearing the cyclopropane carboxylic acid or cyclopropane (thio) carboxylic acid moiety is bonded to the β-position of the naphthalene ring are of high interest.

Preferred compounds of formula I are those wherein X is oxygen. Especially preferred compounds of formula I are those wherein $R_2$ is hydrogen or halogen. Also preferred compounds of formula I are those wherein $R_3$ is hydrogen or methyl in the 6-position of the naphthalene ring.

Especially preferred compounds of formula I are:
cyclopropane carboxylic acid α-2-naphthylbenzyl ester,
cyclopropane carboxylic acid (6-methyl-2-naphthyl)-methyl ester, and
cyclopropane thiolcarboxylic acid 2-naphthylmethyl ester.

The compounds of formula I are prepared by one of the procedures described below.

A. The esterification of the acid of the formula

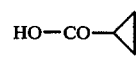

or a reactive derivative thereof with an alcohol or thiolalcohol of the formula

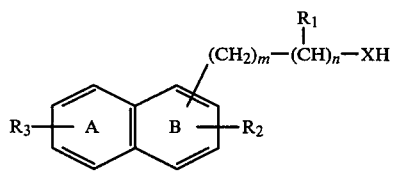

wherein $R_1$, $R_2$, $R_3$, X, A, B, m and n have the significance given above.

The reaction may be carried out, if necessary, in the presence of a base.

The term "reactive derivative of the acid" refers to an acid halide, an acid anhydride, an imidazolide, an ester of a low-boiling alcohol, an alkali metal salt, a silver salt or a salt of a tertiary amine.

The esterification process using the acid of formula II is preferably carried out in a suitable inert solvent, at room temperature or at an elevated temperature. The reaction conditions are such as are suitable for eliminating water, e.g. in the presence of dicyclohexylcarbodiimide or by azeotropically distilling off the water formed in the catalyzed reaction mixture. If an acid halide is used as the reactive derivative of the acid of formula II, The reaction with the alcohol is carried out at room temperature in the presence of an acid acceptor, e.g. a tertiary amine such as pyridine or triethylamine and, preferably, in an inert solvent. The corresponding ester is obtained in high yield.

Preferred acid halides are the acid chlorides. Examples of suitable inert solvents include benzene, toluene and petroleum ether.

If an ester of a low-boiling alcohol is used as the reactive derivative of the acid of formula II the compounds of formula I are prepared by heating the ester with the alcohol or thioalcohol of the formula III in the presence of a base, preferably an alkali metal alcoholate which corresponds to the low-boiling alcohol of the ester employed, or in the presence of sodium hydride in an inert solvent such as toluene. The low-boiling alcohol, liberated during the reaction, is removed by fractional distillation.

Examples of low-boiling alcohols include methanol and ethanol.

If an imidazolide is used as the reactive derivative of the acid of formula II, the compounds of formula I are prepared by reacting the imidazolide with an alkali metal alcoholate of the alcohol or thialcohol of formula III and, if desired, in the presence of a catalytic amount of an alkali metal alcoholate, e.g. sodium ethanolate. The reaction is preferably carried out at room temperature in an inert solvent, such as tetrahydrofuran or dimethoxyethane.

If an acid anhydride is used as the reactive derivative of the acid of the formula II, the compounds of formula I are prepared by reacting the acid anhydride with an alcohol or thioalcohol of formula III at room temperature or, preferably, with heating and in the presence of a solvent such as toluene or xylene.

B. The esterification of the acid of the formula

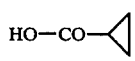

II or the corresponding thiol acid with a compound of the formula

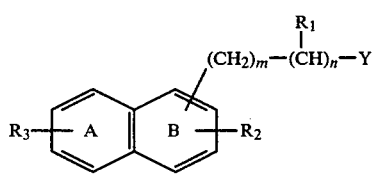

IV wherein $R_1$, $R_2$, $R_3$, A, B, m and n have the significance given earlier and Y is chlorine, bromine, mesyloxy or tosyloxy.

The reaction is conveniently carried out in the presence of a base.

The acid or thiol acid of formula II is reacted with the halide or sulfonic acid ester of formula IV.

The reaction is preferably carried out in an organic solvent. Suitable solvents for the preparation of compounds of formula I in which X is oxygen include, for example, acetone, methyl ethyl ketone, diethyl ketone, dimethylformamide, dimethyl sulfoxide, benzene and toluene. Suitable solvents for the preparation of compounds of formula I in which X is sulphur include, for example, acetone, methyl ethyl ketone, diethyl ketone and alcohol. In both cases, the reaction is conveniently carried out in the presence of a base, preferably potassium carbonate or, especially for the preparation of compounds of formula I in which X is sulphur, an alkali hydroxide such as sodium hydroxide. The reaction is preferably carried out at a temperature between 20° C. and the boiling point of the solvent. After completion of the reaction, the reaction mixture is poured into an inorganic acid, preferably dilute hydrochloric acid, dilute sulfuric acid, dilute phosphoric acid or dilute nitric acid. The acid solution is extracted with hexane or ether, the solvent is distilled off and the residue is purified by chromatography on silica gel or aluminium oxide and/or by distillation.

Some of the starting materials of the formula

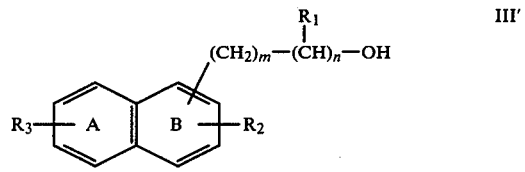

III' wherein $R_1$, $R_2$, $R_3$, A, B, n and m have the significance given earlier, are novel.

Compounds of formula III', wherein n is 1 can be prepared, for example, by reacting a compound of the formula

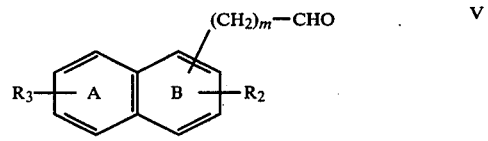

V wherein $R_2$, $R_3$, A, B and m have the significance given earlier, with a Grignard reagent of the general formula $$R_4-MgZ$$

wherein $R_4$ is lower alkyl, lower alkenyl, lower alkynyl, phenyl, substituted phenyl with the substituents selected from the class consisting of halogen, methyl, ethyl, methoxy, ethoxy and nitro, and Z is chlorine, bromine or iodine, under the conditions of a Grignard reaction.

Compounds of formula III' wherein n is zero and m is 1, 2 or 3 can be prepared by reacting an ester of the formula

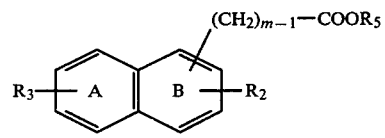

VII wherein $R_2$, $R_3$, m, A and B have the significance given earlier and $R_5$ is lower alkyl, with a complex metal hydride (e.g. lithium aluminium hydride) in an inert organic solvent, preferably diethyl ether or tetrahydrofuran, at a temperature between $-10°$ C. and the boiling point of the mixture.

The starting materials of formula IV are prepared by conversion of the alcohols of formula III'.

For example, an alcohol of formula III′ is treated with thionyl chloride or phosphorus tribromide in an inert solvent (e.g. hexane, benzene or diethyl ether) or with methanesulfonic acid chloride or p-toluenesulfonic acid chloride in an inert solvent (e.g. diethyl ether) in the presence of an acid-binding agent (e.g. pyridine).

The resulting compound of formula IV is then reacted in accordance with embodiment B of the process with a cyclopropane carboxylic acid or the corresponding thiol acid to yield the compound of formula I.

The invention is also directed to pesticidal compositions which comprise inert carrier material and, as the active ingredient, a compound of formula I. These pesticidal compositions contain, as the inert carrier material, at least one of the following ingredients: carrier material, wetting agents, inert diluents and solvents.

The compounds of formula I are, in general, water insoluble. Thus, the usual methods of formulation of insoluble materials can be followed. For example, the compounds of formula I can be dissolved in a water-immiscible solvent such as a high-boiling hydrocarbon which, preferably, contains dissolved emulsifiers. The solution acts as a self-emulsifiable oil when added to water.

The compounds of formula I can also be mixed with a wetting agent, with or without an inert diluent, to form a wettable powder which is soluble or dispersible in water. The compounds can also be mixed with an inert diluent to form a solid or pulverulent powder.

Suitable inert diluents, with which the compounds of the formula I can be processed, are solid inert media including pulverulent or finely divided solids such as clays, sand, talc, mica, fertilizers and the like. The resulting compositions can be either dusts or materials of relatively large particle size.

Wetting agents, suitable for use with the compounds of formula I can be anionic, cationic or non-ionic.

Examples of anionic wetting agents include soaps, fatty sulfate esters such as sodium dodecyl-sulfate, sodium octadecyl-sulfate and sodium cetyl-sulfate, fatty-aromatic sulfonates, such as alkylbenzene-sulfonates, or butylnaphthalene-sulfonates, and the more complex fatty sulfonates, such as the amide condensation products of oleic acid and N-methyltaurine or the sodium salt of sulfosuccinic acid bis-2-ethylhexyl ester.

Examples of cationic wetting agents include cetyl-trimethylammonium chloride and the like.

Examples of non-ionic wetting agents include, for example, condensation products of fatty acids, fatty alcohols or fatty-alkyl-substituted phenols with ethylene oxide, fatty acid esters and ethers of sugars or of polyhydric alcohols, condensation products of these fatty acid esters and ethers of sugars or of polyhydric alcohols with ethylene oxide or block copolymers of ethylene oxide and propylene oxide.

The pesticidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

The pesticidal compositions of this invention can also contain other active ingredients such as synergistic agents and other insecticides, bactericides and fungicides.

The compounds of formula I are particularly valuable as insecticides and acaricides especially against sucking pests such as white flies, aphids and spiders such as tetranychidae, eriophyidae and ixodoidea. The compounds act as direct insecticides and mainly as direct ovicides. They thus reduce, on a long term basis, any increase in the insect population. The compounds of formula I also possess systemic action. Their action as acaricides is a preferred aspect of this invention.

The present invention is also concerned with a method for the treatment of animals and locus, e.g. plants, soil, objects and surfaces subject to or subjected to attack by pests free from such attack, which method comprises applying to said animals or locus an effective amount of the pesticidal composition as defined hereinabove.

In general, the compounds of formula I can be used in different concentrations depending on its intended use. For example, the compounds are applied at a concentration of about 100 to about 2,000 g/ha for combatting pests on plants. To combat ectoparasites on animals, the animals are conveniently dipped in a solution containing from about 100 to about 1,000 ppm of a compound of formula I. Alternatively, the animals can be sprayed with a solution of the same concentration.

The acute toxicities of the compounds of formula I are greater than 1,000 mg/kg. Thus, they are of extremely low toxicity to vertebrae.

The compounds of formula I also have a high ultraviolet stability.

The following Examples illustrate the invention.

EXAMPLE 1

Two g of 1-hydroxymethylnaphthalene are dissolved in 20 ml of benzene and 0.7 ml of pyridine. 1.2 ml of cyclopropane carboxylic acid chloride in 10 ml of benzene are then added and the mixture is heated at 70° C. for 15 minutes. The resulting product is poured into water and extracted with ether. The ether extract is washed with water, dried over sodium sulfate and evaporated under reduced pressure. The residual cyclopropane carboxylic acid 1-naphthylmethyl ester is purified by adsorption on silica gel; $n_D^{20} = 1.5924$.

In an analogous manner, cyclopropane carboxylic acid 2-(2-naphthyl)ethyl ester, $n_D^{20} = 1,5855$, is prepared from 1-naphthylethanol and cyclopropane carboxylic acid chloride;

cyclopropane carboxylic acid 2-(2-naphthyl)ethyl ester, $n_D^{20} = 1.5758$, is prepared from 2-naphthylethanol and cyclopropane carboxylic acid chloride;

cyclopropane carboxylic acid (1,2,3,4-tetrahydro-2-naphthyl)-methyl ester, $n_D^{20} = 1.5370$, is prepared from (1,2,3,4-tetrahydro-2-naphthyl)methanol and cyclopropane carboxylic acid chloride;

cyclopropane carboxylic acid 1-(2-naphthyl)ethyl ester, $n_D^{20} = 1.5760$, is prepared from 1-(2-naphthyl)ethanol and cyclopropane carboxylic acid chloride;

cyclopropane carboxylic acid (2-decahydronaphthyl)-methyl ester, $n_D^{25} = 1.5355$, is prepared from (2-decahydronaphthyl)methanol and cyclopropane carboxylic acid chloride;

cyclopropane carboxylic acid 3-(5,6,7,8-tetrahydro-1-naphthyl)propyl ester, $n_D^{25} = 1.5375$, is prepared from 3-(5,6,7,8-tetrahydro-1-naphthyl)propanol and cyclopropane carboxylic acid chloride.

cyclopropane carboxylic acid (1-bromo-2-naphthyl)-methyl ester, $n_D^{20} = 1.5940$, is prepared from (1-bromo-2-naphthyl)methanol and cyclopropane carboxylic acid chloride;

cyclopropane carboxylic acid (3-methoxy-2-naphthyl)-methyl ester, $n_D^{20} = 1.5890$, is prepared from (3- methoxy-2-naphthyl)methanol and cyclopropane carboxylic acid chloride;

cyclopropane carboxylic acid (5,6,7,8-tetrahydro-2-naphthyl)-methyl ester, $n_D^{25} = 1.5355$, is prepared from 5,6,7,8-tetrahydro-2-naphthyl)methanol and cyclopropane carboxylic acid chloride;

cyclopropane carboxylic acid (4-bromo-1-naphthyl)-methyl ester, melting point 55°–56° C., is prepared from (4-bromo-1-naphthyl)methanol and cyclopropane carboxylic acid chloride;

cyclopropane carboxylic acid (2-methoxy-1-naphthyl)-methyl ester, melting point 62°–63° C., is prepared from (2-methoxy-1-naphthyl)methanol and cyclopropane carboxylic acid chloride;

cyclopropane carboxylic acid (1-methoxy-2-naphthyl)-methyl ester, $n_D^{20} = 1.5857$, is prepared from (1-methoxy-2-naphthyl)methanol and cyclopropane carboxylic acid chloride;

cyclopropane carboxylic acid (6-methoxy-2-naphthyl)-methyl ester, melting point 81°–83° C., is prepared from (6-methoxy-2-naphthyl)methanol and cyclopropane carboxylic acid chloride, and cyclopropane carboxylic acid 2,2,2-trichloro-1-(2-naphthyl)ethyl ester, melting point 108°–109° C., is prepared from α-(trichloromethyl)-2-naphthalenemethanol and cyclopropane carboxylic acid chloride.

EXAMPLE 2

3.6 g of 1-(2-naphthyl)-2-propyn-1-ol and 1.6 g of pyridine are dissolved in 30 ml of methylene chloride, the solution is cooled to 0°–5° C. and a solution of 2.3 g of cyclopropane carboxylic acid chloride in 10 ml of methylene chloride is added with stirring. The mixture is left at room temperature for 2 hours, then poured into water and diluted with 50 ml of methylene chloride. The methylene chloride solution is separated and washed, in sequence, with 2 N hydrochloric acid solution, 10% potassium bicarbonate solution and a semi-saturated sodium chloride solution. The solution is then dried over sodium sulfate and evaporated. The crude product is purified by crystallization or by adsorption chromatography on silica gel to yield pure cyclopropane carboxylic acid 1-(2-naphthyl)-2-propynyl ester, m.p. 94°–96° C. (from cyclohexane).

In an analogous manner, cyclopropane carboxylic acid α-cyano-2-naphthylmethyl ester, melting point 65°–66° C., is prepared from 2-naphthaldehyde cyanohydrin and cyclopropane carboxylic acid chloride;

chcloropane carboxylic acid 2-methyl-1-(2-naphthyl)-propyl ester, melting point 35°–37° C., is prepared from α-isopropyl-2-naphthalenemethanol and cyclopropane carboxylic acid chloride, and cyclopropane carboxylic acid α-2-naphthylbenzyl ester, $n_D^{20} = 1.6004$, is prepared from α-phenyl-2-naphthalenemethanol and cyclopropane carboxylic acid chloride.

EXAMPLE 3

1.89 g of cyclopropane carboxylic acid are dissolved in 50 ml of acetone, treated with 5.5 g of potassium carbonate and heated to 50° C. A solution of 4.7 g of 6-methyl-2-(bromomethyl)naphthalene in 20 ml of acetone is then added dropwise. The mixture is left to react at 65° C. for 15 hours. The mixture is cooled and filtered. The residue is then rinsed with acetone and the filtrate is evaporated. The residue is purified chromatography on silica gel with hexane/ethyl acetate (9:1) to yield pure cyclopropane carboxylic acid (6-methyl-2-naphthyl)methyl ester of melting point 75°–78° C. (from petane/ether).

In an analogous manner, cyclopropane carboxylic acid (3-methyl-2-naphthyl)-methyl ester, melting point 60°–61° C. (from hexane), is prepared from 3-methyl-2-(bromomethyl)naphthalene and cyclopropane carboxylic acid.

EXAMPLE 4

3.28 g of magnesium are treated with an iodine crystal and covered with absolute diethyl ether. The reaction is started by the addition of 2 g of allyl bromide. A mixture of 19.78 g of allyl bromide and 15.62 g of 2-naphthaldehyde in absolute diethyl ether is then added dropwise to maintain the mixture at reflux. After the addition is completed, the mixture is left to stir at room temperature overnight. The mixture is poured into an ice - 2 N hydrochloric acid solution and extracted three times with ether. The ether extracts are washed with water and saturated sodium chloride solution, dried over sodium sulfate and evaporated to yield 1-(2-naphthyl)-3-buten-1-ol which can be used without further purification for the reaction with cyclopropane carboxylic acid chloride in the process of Example 2. The resulting product is cyclopropane carboxylic acid 1-(2-naphthyl)-3-butenyl ester, m.p. 35°–39° C.

EXAMPLE 5

1.8 g of magnesium are covered with 10 ml of absolute tetrahydrofuran. About 1 ml of a solution of 8 g of vinyl bromide in 8 ml of absolute tetrahydrofuran is added dropwise and the reaction is initiated by slight warming. Then, the remainder of the vinyl bromide solution is added dropwise. The mixture is left to react until it reaches room temperature. A solution of 7 g of 2-naphthaldehyde in 50 ml of absolute tetrahydrofuran is then added slowly dropwise, as the temperature rises to 40° C. The reaction is completed within 1 hour. The mixture is then hydrolyzed by the addition with stirring of 20 ml of saturated ammonium chloride solution at 0° C. The residue is filtered and rinsed with ether. The filtrate is diluted with water and extracted twice with ether. The ether extracts are washed with semi-saturated and saturated sodium chloride solution, dried over sodium sulfate and evaporated to yield 1-(2-naphthyl)-2-propen-1-ol which, without further purification, is esterified with cyclopropane carboxylic acid chloride in the process of Example 2. The resulting product is cyclopropane carboxylic acid 1-(2-naphthyl)allyl ester of melting point 30°–32° C.

EXAMPLE 6

6.5 g of 6-methoxy-2-naphthaldehyde are treated with a solution of 4.28 g of sodium cyanide in 115 ml of 95% ethanol. 11.5 ml of acetic acid are then added dropwise at 0° C. over a period of 1 hour. The mixture is left to react overnight and then 400 ml of water are needed. The mixture is extracted three times with ether, the ether extracts are washed with 10% potassium bicarbonate solution and semisaturated and saturated sodium chloride solution. The extracts are dried over sodium sulfate and evaporated to yield α-cyano-(6-methoxy-2-naphthyl)methanol which, without further purification, is reacted with cyclopropane carboxylic acid chloride in the process of Example 2. The resulting product is cyclopropane carboxylic acid α-cyano-(6-methoxy-2-naphthyl)methyl ester; $n_D^{20} = 1.5765$.

EXAMPLE 7

14.55 g of 1-(2-propynyloxy)-naphthoic acid 2-propynyl ester dissolved in 50 ml of absolute tetrahydrofuran are cautiously added at −10° C. under a nitrogen atmosphere to a suspension of 2.09 g of lithium aluminum hydride in 200 ml of absolute tetrahydrofuran. After completion of the addition is complete, the mixture is left to react at about 0° C. for a further 1 hour. To hydrolyze, water is cautiously added dropwise at −10° C. with stirring while the temperature is maintained at 0° C. or below. The mixture is filtered using a filter aid (Celite) and the filtrate is concentrated. The residue is dissolved in ethyl acetate and washed, in sequence, with 2 N hydrochloric acid solution, 10% potassium bicarbonate solution, semi-saturated and saturated sodium chloride solution. The residue is dried over sodium sulfate and evaporated. Pure [1-(2-propynyloxy)-2-naphthyl]methanol, m.p. 65°–68° C. (from hexane/ethyl acetate), is obtained by recrystallization. This material is reacted with cyclopropane carboxylic acid chloride in the procedure described in Example 2 to yield cyclopropane carboxylic acid [1-(2-propynyloxy)-2-naphthyl]methyl ester; $n_D^{20} = 1.5902$.

EXAMPLE 8

20.2 g of 3-hydroxy-2-naphthoic acid methyl ester are dissolved in 200 ml of methyl ethyl ketone and 27.6 g of potassium carbonate and 23.6 g of propargyl bromide are added thereto with stirring and under a nitrogen atmosphere. The heterogeneous mixture is refluxed overnight and then filtered. The filtrate is concentrate in vacuo and the residue is poured into 250 ml of ice-water and extracted three times with hexane/ethyl acetate (1:1). The extracts are washed with 2 N hydrochloric acid solution, 10% potassium bicarbonate solution, semi-saturated and saturated sodium chloride solution, dried and evaporated on a rotary evaporator. The product 3-(2-propynyloxy)-2-naphthoic acid methyl ester is reduced, without further purification, with lithium aluminum hydride by the process described in Example 7. The resulting [3-(2-propynyloxy)-2-naphthyl]methanol is reacted directly with cyclopropane carboxylic acid chloride by the process described in Example 2 to yield cyclopropane carboxylic acid [3-(2-propynyloxy)-2-naphthyl]methyl ester of melting point 58°–60° C.

EXAMPLE 9

2-(2-Propynyloxy)-1-naphthaldehyde and lithium aluminum hydride are reacted by the process described in Example 7 to form [2-(2-propynyloxy-1-naphthyl]-methanol (melting point 37°–43° C.). This compound is reacted with cyclopropane carboxylic acid chloride by a process analogous to that described in Example 2 to yield cyclopropane carboxylic acid [2-(2-propynyloxy)-1-naphthyl]methyl ester of melting point 68°–73° C.

EXAMPLE 10

4.0 g of 2-naphthylmethylthiol and 2.4 g of cyclopropane carboxylic acid chloride are added to 50 ml of toluene. 2.4 g of triethylamine in 20 ml of toluene are added dropwise. The mixture is then heated at 85° C. for 20 hours. After the reaction, the mixture is poured into water and extracted with ether. The ether extract is washed with water, dried over sodium sulfate, filtered and evaporated. The residue is purified by chromatography on silica gel with hexane/ether (19:1) to yield pure cyclopropane thiolcarboxylic acid 2-naphthylmethyl ester of melting point 39°–40° C.

In analogous manner, cyclopropane thiolcarboxylic acid 1-naphthylmethyl ester, $n_D^{25} = 1.3359$, is prepared from 1-naphthylmethylthiol and cyclopropane carboxylic acid chloride.

EXAMPLE 11

2.6 g of cyclopropane carboxylic acid chloride are added over 5 minutes to a solution of 2.0 g of sodium hydrogen sulfide in 20 ml of ethanol which is cooled in ice. After 30 minutes, 5.5 g of 2-bromomethylnaphthalene are added. Then 10 ml of 10% sodium hydroxide are slowly added dropwise at room temperature. After 1 hour stirring at room temperature, 25 ml of dichloromethane are added and the solution is washed twice with 10% potassium bicarbonate solution and saturated sodium chloride solution, dried over sodium sulfate and evaporated. The residue is purified by chromatography on silica gel to yield pure cyclopropane thiolcarboxylic acid 2-naphthylmethyl ester.

EXAMPLE 12

By a process analogous to that of Example 3, cyclopropane carboxylic acid (1-nitro-2-naphthyl)methyl ester, m.p. 84°–86° C., is prepared from cyclopropane carboxylic acid and 1-nitro-2-(bromomethyl)-naphthalene.

The starting material, 1-nitro-2-(bromomethyl)-naphthalene, is prepared by heating to boiling, using a photo lamp, a mixture of 18.7 g of 2-methyl-1-nitronaphthalene, 17.8 g of N-bromosuccinimide, 400 ml of carbon tetrachloride and 0.1 g of dibenzoyl peroxide. After the reaction is completed, the mixture is cooled and filtered under suction. The filtrate is poured into water and extracted with methylene chloride. The extracts are washed, in sequence, with 10% sodium hydroxide, water and sodium chloride solution, dried over sodium sulfate and evaporated. The product, crude 1-nitro-2-(bromomethyl)-naphthalene, is used in the reaction with cyclopropane carboxylic acid.

EXAMPLE 13

This Example illustrates the preparation of an emulsifiable concentrate and a sprayable powder using the compounds of formula I by admixture of the following ingredients.

| Emulsifiable Concentrate | g/l |
| --- | --- |
| Active ingredient, compound of formula I | 500 |
| Mixture of castor oil/ethylene oxide condensation product with ca 25 mol ethylene oxide and calcium dodecyl benzensulfonate in the ratio 3:1 | 100 |
| Epoxidated soya oil with an oxirane oxygen content of 6% | 25 |
| Butylated hydroxytoluene | 10 |
| Solvent consisting of a mixture of mono-, di- and tri(lower alkyl)benzenes - to | 1000 ml |
| Sprayable Powder | |
| Active ingredient, compound of formula I | 50 |
| Hydrated silicic acid | 37 |
| Maleic acid-diisobutylene copolymer sodium salt | 4 |
| Nonylphenol ethoxylate | 4 |
| Kaolin | 5 |
| | 100.0 g |

In the Examples that follow, the active ingredients, the compounds of formula I, are identified by the Roman numerals listed below.

| | |
|---|---|
| I | Cyclopropane carboxylic acid 1-naphthylmethyl ester. |
| II | Cyclopropane carboxylic acid 2-(1-naphthyl)ethyl ester. |
| III | Cyclopropane carboxylic acid 2-(2-naphthyl)ethyl ester. |
| IV | Cyclopropane carboxylic acid (5,6,7,8-tetrahydro-2-naphtyl)methyl ester. |
| V | Cyclopropane carboxylic acid (1,2,3,4-tetrahydro-2-naphthyl)methyl ester. |
| VI | Cyclopropane carboxylic acid 1-(2-naphthyl)ethyl ester. |
| VII | Cyclopropane carboxylic acid (decahydro-2-naphthyl)methyl ester. |
| VIII | Cyclopropane carboxylic acid (2-methoxy-1-naphthyl)methyl ester. |
| IX | Cyclopropane carboxylic acid [2-(2-propynyloxy)-1-naphthyl]methyl ester. |
| X | Cyclopropane carboxylic acid (1-methoxy-2-naphthyl)methyl ester. |
| XI | Cyclopropane carboxylic acid 3-(5,6,7,8-tetrahydro-1-naphthyl)propyl ester. |
| XII | Cyclopropane carboxylic acid α-cyano-2-naphthylmethyl ester. |
| XIII | Cyclopropane carboxylic acid 1-(2-naphthyl)-2-propynyl ester. |
| XIV | Cyclopropane carboxylic acid (6-methoxy-2-naphthyl)methyl ester. |
| XV | Cyclopropane carboxylic acid 2,2,2-trichloro-1-(2-naphthyl)ethyl ester. |
| XVI | Cyclopropane carboxylic acid 1-(2-naphthyl)-3-butenyl ester. |
| XVII | Cyclopropane carboxylic acid (4-bromo-1-naphthyl)methyl ester. |
| XVIII | Cyclopropane carboxylic acid (3-methoxy-2-naphthyl)methyl ester. |
| XIX | Cyclopropane carboxylic acid α-2-naphthylbenzyl ester. |
| XX | Cyclopropane carboxylic acid (6-methyl-2-naphthyl)methyl ester. |

EXAMPLE 14

This Example illustrates the activity of compounds of formula I on common spider mites (*Tetranychus urticae*).

Bush bean leaf roundels, infected with 20 mobile spider mites, were sprayed (at rates of $10^{-5}$ and $10^{-6}$ g of active ingredient per cm$^2$) with a solution of the active ingredient in acetone. The treated leaf roundels were placed on moist foam material and incubated at 25° C. and 60% relative humidity. Untreated roundels and roundels treated with acetone were used as the controls. Afer 3 days, the leaf roundels were examined for the number of spider mites.

The results, reported in the Table below, are expressed as the percent reduction in the survival rate of the mites in comparison to the controls.

| | Percent Reduction in Survival Rate Dosage ($10^{-x}$g AI/cm$^2$): | |
|---|---|---|
| Active Ingredient | 5 | 6 |
| I | 100 | 0 |
| II | 100 | 0 |
| III | 100 | 0 |
| IV | 100 | 7 |
| V | 100 | 21 |
| VI | 97 | 2 |
| VII | 100 | 6 |
| VIII | 100 | 0 |
| IX | 100 | 3 |
| X | 100 | 14 |
| XI | 100 | 8 |
| XII | 100 | 18 |
| XIII | 100 | 40 |
| XIV | 100 | 48 |
| XV | 100 | 20 |
| XVI | 100 | 1 |
| XVII | 100 | 0 |

(Mortality in untreated controls: 5%)
AI = Active Ingredient

EXAMPLE 15

This Example illustrates the activity of compounds of formula I on common spider mite (*Tetranychus urticae*).

Young bush bean plants (2 leaf stage) were sprayed (at rates of $10^{-5}$, $10^{-6}$ and $10^{-7}$ g of active ingredient per cm$^2$) with a solution of the active substance in acetone. After the spray treatment, the plants were incubated under UV-light (Philips TLA 40W/05) for 7 days at 28° C. and 60% relative humidity. Then 8-10 adult females were placed on roundels (φ25 mm) stamped out from the leaves. One day later the females were removed and the roundels carrying 30-50 eggs were incubated at 25° C. and 60% relative humidity until the larvae hatched. Untreated plants and plants treated with acetone (or roundels therefrom) were used as the controls. The total test duration was 13 days-7 days preincubation under UV-light plus 6 days incubation. The results, reported below, are expressed as the percent reduction in the survival rate of the eggs in comparison to the controls.

| | Percent Reduction in Survival Rate- Dosage ($10^{-x}$g AI/cm$^2$): | | |
|---|---|---|---|
| Active Ingredient | 5- | 6 | 7 |
| VI | 100 | 0 | — |
| XI | 94 | 0 | — |
| XII | 100 | 0 | — |
| XIII | 100 | 0 | — |
| XIV | 100 | 94 | 13 |
| XVI | 100 | 32 | 0 |
| XVII | 88 | 0 | — |
| XVIII | 100 | 0 | — |
| XIX | 100 | 100 | 0 |
| XX | 100 | 100 | 0 |

(Mortality in untreated controls: 3%)

EXAMPLE 16

A composition containing a compound of formula I can be formulated as follows:

| | g/liter |
|---|---|
| Active ingredient, compound of formula I | 500 |
| N-Methyl-2-pyrrolidone | 300 |
| Emulsifier moxture of calcium alkylaryl sulfonate, alkylphenol ethoxylate, block polymerisate of propylene oxide and ethylene oxide | 100 |
| Calcium dodecylbenzenesulfonate | 25 |
| Solvent consisting of a mixture of mono-, di- and tri(lower alkyl)-benzenes to | 1000 ml |

The active ingredients used in the following Examples are identified as follows:

| Active-Ingredient | Structural formula |
|---|---|
| Compound I | 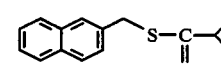<br>Cyclopropane thiol-carboxylic acid 2-naphthylmethyl ester |
| Compound A (ZARDEX) [standard] | 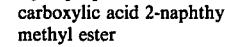<br>Cyclopropane carboxylic acid hexadecyl ester |
| Compound B (Thionazin, NEMAFOS) [Standard] | <br>O-(2-Pyrazinyl)-thiophosphoric acid O,O-diethyl ester |

EXAMPLE 17

This Example compares the activity of a compound of formula I with a standard insecticide against the common spider (*Tetranychus urticae*).

The test procedure followed as described in Example 15. Results are reported below as the percent reduction in the survival rate.

| | Percent Reduction in Survival Rate Dosage ($10^{-x}$g AL/cm$^2$); | | |
|---|---|---|---|
| Active Ingredient | 5 | 6 | 7 |
| Compound I | 98 | 78 | 22 |
| Compound A | 100 | 0 | 0 |

(Mortality in untreated controls: 3%)

EXAMPLE 18

This Example compares the activity of a compound of formula I with a standard insecticide against the white fly (*Trialeurodes vaporariorum*).

Bush bean leaf roundels (diameter 25 mm) carrying eggs (0–15 hours old) were sprayed with a solution of the active substance in acetone. The leaf roundels were placed on moist filter paper and incubated at 25° C. and 60% relative humidity until the larvae hatched. Untreated roundels and roundels treated with acetone were used as the controls. After 9 days, the leaf roundels were examined for the number of larvae. The results are expressed as the percent reduction in the survival rate in comparison to the controls.

| | Percent Reduction in Survival Rate Dosage $10^{-x}$g AI/cm$^2$): | | | |
|---|---|---|---|---|
| Active Ingredient | 5 | 6 | 7 | 8 |
| Compound I | 100 | 100 | 52 | 0 |
| Compound B | 23 | 0 | 0 | — |

(Mortality in untreated controls: 12%).

I claim:

1. A compound of the formula

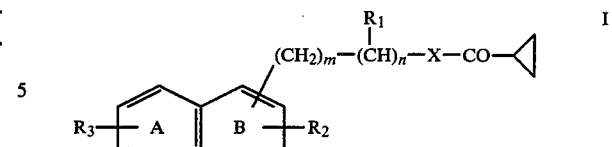

wherein $R_1$ is lower alkyl, halo-substituted lower alkyl, lower alkenyl, lower alknyl, cyano, phenyl, substituted phenyl wherein the substituents are selected from the group consisting of halogen, methyl, ethyl, methoxy, ethoxy and nitro; $R_2$ is hydrogen, halogen, alkyl of from 1 to 3 carbons, alkoxy of from 1 to 3 carbons, alkenyloxy of 3 or 4 carbons, alkynyloxy of 3 or 4 carbon or nitro; $R_3$ is hydrogen, alkyl of from 1 to 3 carbons or alkoxy of from 1 to 3 carbons; X is sulphur; m is zero or an integer of from 1 to 3 and n is zero or 1; wherein one or both of rings A and B can be saturated and wherein m and n cannot simultaneously be zero.

2. A compound of claim 1 wherein $R_2$ is hydrogen or halogen.

3. A compound of claim 1 wherein $R_3$ is hydrogen or methyl in the 6-position of the naphthalene ring.

4. A compound of claim 1, cyclopropane thiocarboxylic acid 2-naphthyl methyl ester.

5. A compound of claim 1, cyclopropane thiocarboxylic acid 1-naphthylmethyl ester.

6. A pesticidal composition which comprises inert carrier material and, as the active ingredient, an amount which is effective as a pesticide of at least one compound of the formula

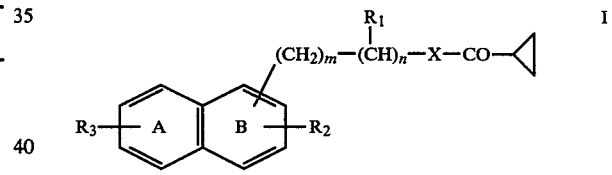

wherein $R_1$ is lower alkyl, halo-substituted lower alkyl, lower alkenyl, lower alkynyl, cyano, phenyl, substituted phenyl wherein the substituents are selected from the group consisting of halogen, methyl, ethyl, methoxy, ethoxy and nitro; $R_2$ is hydrogen, halogen, alkyl of from 1 to 3 carbons, alkoxy of from 1 to 3 carbons, alkenyloxy of 3 or 4 carbons, alkynyloxy of 3 or 4 carbons or nitro; $R_3$ is hydrogen, alkyl of from 1 to 3 carbons or an alkoxy of from 1 to 3 carbons; X is sulphur; m is zero or an integer of from 1 to 3 and n is zero or 1; wherein one or both rings A and B can be saturated and wherein m and n cannot simultaneously be zero.

7. The pesticidal composition of claim 6 wherein the active ingredient is cyclopropane thiocarboxylic acid 2-naphthylmethyl ester.

8. A method for combatting pests which comprises treating the animal, plant or locus to be protected with a pesticidal effective amount of the composition of claim 6.

9. A method for combatting pests which comprises application of a pesticidal effective amount of the composition of claim 6 to the pests.

* * * * *